United States Patent [19]
Block

[11] Patent Number: 6,002,953
[45] Date of Patent: Dec. 14, 1999

[54] NON-INVASIVE IR TRANSMISSION MEASUREMENT OF ANALYTE IN THE TYMPANIC MEMBRANE

[75] Inventor: Myron J. Block, Jupiter Island, Fla.

[73] Assignee: Optix LP, Jupiter Island, Fla.

[21] Appl. No.: 09/073,574

[22] Filed: May 6, 1998

[51] Int. Cl.[6] ........................................ A61B 5/00
[52] U.S. Cl. .......................... 600/316; 600/341
[58] Field of Search ................... 600/310, 316, 600/322, 341, 342, 325, 327, 339, 473

[56] References Cited

U.S. PATENT DOCUMENTS

| | | | |
|---|---|---|---|
| 3,958,560 | 5/1976 | March | 128/2 |
| 4,014,321 | 3/1977 | March | 128/2 |
| 5,028,787 | 7/1991 | Rosenthal et al. | 250/341 |
| 5,146,091 | 9/1992 | Knudson | 250/341 |
| 5,179,951 | 1/1993 | Knudson | 128/633 |
| 5,321,265 | 6/1994 | Block | 250/343 |
| 5,424,545 | 6/1995 | Block et al. | 250/343 |
| 5,434,412 | 7/1995 | Sodickson et al. | 250/343 |
| 5,515,847 | 5/1996 | Braig et al. | 128/633 |
| 5,615,672 | 4/1997 | Braig et al. | 128/633 |
| 5,638,816 | 6/1997 | Kiani-Azarbayjany et al. | 128/633 |
| 5,666,956 | 9/1997 | Buchert | 128/664 |
| 5,672,875 | 9/1997 | Block et al. | 250/343 |

OTHER PUBLICATIONS

Arnold, M. and Small, G., "Determination of Physiological Levels of Glucose in an Aqueous Matrix with Digitally Filtered Fourier Transform Near–Infrared Spectra," *Analytical Chemistry*, vol. 62, No. 14, 1457–64 (1990).

Dufort, P.A. and Lumsden, C.J., "Color Categorization and Color Constancy in a Neural Network Model of V4," *Biological Cybernetics*, vol. 65, 293–303 (1991).

Mendelson, Y. et al., "Blood Glucose Measurement by Multiple Attenuated Total Reflection and Infrared Absorption Spectroscopy," *IEEE Transactions on Biomedical Engineering*, vol. 37, No. 5, 458–65 (1990).

Moore, A. et al., "A Real–Time Neural System for Color Constancy," *IEEE Transactions on Neural Networks*, vol. 2, No. 2, 237–47 (1991).

*Primary Examiner*—Eric F. Winakur
*Attorney, Agent, or Firm*—Lahive & Cockfield, LLP

[57] ABSTRACT

The invention provides non-invasive methods and apparati for measurement of the concentration of a selected constituent of a subject's blood. The invention cools a segment of the subject's tympanic membrane and employs the thermal radiation that the subject's inner ear emits and is transmitted through this cold segment to directly obtain absorption information related to the concentration of various constituents of blood flowing through the membrane. In particular the invention utilizes optical devices inserted into the external ear cavity to direct a portion of the transmitted radiation onto an infrared detection and analysis device. The signal from the detection device is analyzed to obtain the concentration of the constituent of interest. The invention can employ both traditional spectrophotometric techniques and also non-spectrophotometric techniques to derive the concentration of a particular constituent.

30 Claims, 4 Drawing Sheets

NON-INVASIVE IR TRANSMISSION MEASUREMENT OF ANALYTE IN THE TYMPANIC MEMBRANE

BACKGROUND

This invention relates generally to methods and apparatus for non-invasive determination of the concentration of particular constituents of a patient's blood. In particular, the invention determines the concentration of constituents such as glucose, and other clinical analytes without providing an external radiation source. The invention can be utilized to measure the concentration of such analytes both in clinical settings and also at home, e.g., home glucose testing.

The non-invasive determination of various constituents of blood provides distinct advantages over traditional invasive procedures. The invasive techniques expose patients to various contaminants in the environment which can potentially lead to contracting diseases such as AIDS or hepatitis B if adequate safety precautions for the use of the invasive methods are not taken. Non-invasive techniques eliminate such potentially harmful exposures and can play important roles in the management of many patients, e.g., diabetic patients. Diabetic patients who need to monitor the glucose content of their blood on a regular basis, typically several times a day, have traditionally employed the finger prick technique for obtaining a blood sample. This technique is not only painful but it also exposes such patients to contaminants in the environment. Patients with artificial heart valves comprise another group of individuals who need to monitor the concentration of various constituents of their blood. For example, such patients may require monitoring of particular constituents in order to properly adjust the intake level of blood-thinning medication. Accordingly, all these individuals can benefit from a non-invasive technique for measuring the concentration of various constituents of blood that is safe and easy to use.

Many issued patents disclose the use of radiation for the non-invasive determination of the glucose concentration of blood. For example, U.S. Pat. No. 3,958,560 discloses an apparatus for the non-invasive measurement of the glucose content of a patient's blood. The disclosed apparatus scans the patient's eye by using a source of radiation located at one side of the patient's cornea and detects the radiation after it passes through the cornea by a sensor located on the other side. The intensity of the transmitted radiation is then correlated to the concentration of glucose. U.S. Pat. No. 4,014,321 discloses a non-invasive glucose sensing device that employs a polarized source of infrared radiation, and correlates the level of glucose in the cornea of a patient to the degree of the rotation of the plane of polarization of the radiation as it passes through the cornea.

The limitations of the invasive techniques in combination with a heightened sense of concern in regard to spread of diseases such as AIDS, have led to a resurgence of interest in developing non-invasive optical techniques in the past several years. For example, U.S. Pat. No. 5,028,787 of Rosenthal et al. discloses a non-invasive apparatus for measuring the glucose content of blood. In particular, Rosenthal et al. measure the intensity of IR radiation transmitted through a subject's blood at a plurality of wavelengths. Rosenthal et al.'s invention obtains the intensity of the transmitted radiation at least one pair of wavelengths, selected such that one is sensitive to glucose absorption and the other is not, and correlates these measurements to the concentration of glucose.

U.S. Pat. No. 5,321,265, herein incorporated by reference, discloses a non-invasive technique that employs a radiation source with a broad band spectrum in the near infrared region, e.g., 700–1100 nm, to illuminate a sample, e.g., a body part, and detects the reflected or transmitted radiation by a plurality of overlapping detection spectral responses. This invention also employs a detection system analogous to that used in color vision to create a vector whose different components relate to the measured intensity of the reflected or transmitted radiation in a particular range of wavelength.

U.S. Pat. No. 5,434,412, herein incorporated by reference, provides improvements on apparatus and methods disclosed in the aforementioned '265 patent. In particular, this patent arranges the apparatus to achieve congruent sampling, i.e., each detector receives radiation from substantially the same portion of the sample transmitted or reflected in the same direction. This results in a better signal-to-noise ratio, thus improving the accuracy of the resultant value of the concentration of the analyte of interest.

U.S. Pat. No. 5,424,545, herein incorporated by reference, employs techniques similar to those disclosed in the aforementioned '265 patent to obtain the concentration of a selected constituent of interest. It, however, differs from the '265 patent in that it employs a plurality of broad-band partially overlapping infrared radiation sources rather than a plurality of detectors with partially overlapping responses.

U.S. Pat. No. 5,666,956 discloses methods and apparatus for collecting naturally emitted thermal radiation from a body part, and for analyzing such radiation for the fingerprints of a particular analyte. In particular, the patent claims that the ratio of the emissivity of the tympanic membrane and the emissivity of a black body at the same temperature as that of the tympanic membrane can be utilized to measure the concentration of an analyte such as glucose.

U.S. Pat. Nos. 5,515,847 and 5,615,672 disclose methods and apparatus for non-invasive measurement of certain blood constituents of a subject by monitoring long-wavelength infrared radiation emitted by the subject's body, preferably from a vascularized appendage. The methods of these patents do not teach the use of a well-defined transmission sample pathlength that is optically separate and thermally isolated from the source of radiation. The accuracy and universality of the calibration of the measurement of the absolute concentration of an analyte in these patents is dependent, in part, on how well-defined is the optical pathlength of the absorbing sample. The disclosed methods do not define the value of the pathlength from where the infrared emissions originate to where they are detectable. Because the disclosed methods utilize radiation originating in a thick piece of tissue, i.e., a wrist, obtaining accurate values of the pathlength is problematic due to multiple scattering of the radiation within the tissue before reaching the detector, and also the uncertainty associated with the place within the tissue where the emitted radiation originates.

The present invention provides improvements over these and other prior art techniques for non-invasive determination of the concentration of a constituent of blood. In particular, the prior art techniques typically rely on transmission of radiation through a fairly thick piece of tissue, e.g., finger tip, which results in an attenuated intensity of transmitted radiation, thereby limiting the choice of wavelengths. Further, a majority of the disclosed non-invasive techniques employ an external radiation source to illuminate a part of a patient's body and at least a detector to measure a portion of the radiation that is transmitted through or reflected from this body part. The use of an external radiation source adds to the complexity and the expense of constructing non-invasive testing devices. In addition, many of the disclosed methods employ traditional spectroscopic analysis for obtaining the concentration of a selected constituent of blood. Although such traditional techniques are suitable for the analysis of spectra that exhibit a multiplicity of highly-resolved bands, they are not particularly appropriate for discriminating broad absorption bands, characteristic of many constituents of blood, from the background noise. In addition, the potential overlap of absorption bands of various constituents, e.g., glucose, fat, proteins, presents another difficulty for the traditional techniques.

Accordingly, it is an object of the present invention to provide methods and apparatus for the non-invasive determination of selected constituents of blood by employing either spectrally overlapping detector responses or traditional spectroscopic methods and without relying on external radiation sources.

It is another object of the invention to collect a portion of the thermal radiation that originates from a subject's inner ear after it passes through a cold segment of the tympanic membrane.

It is yet another object of the invention to take advantage of the thinness of the tympanic membrane to employ regions of spectral wavelengths not available for the measurement of constituents of blood of thicker body parts because of the opacity of these parts to such wavelengths.

It is yet another object of the present invention to provide methods and apparatus for the non-invasive determination of the concentration of selected constituents of a subject's blood by analyzing a portion of the thermal radiation emitted by the subject's inner ear that has passed through the colder tympanic membrane, thus exhibiting the spectral absorption characteristics of the subject's blood in the tympanic membrane.

SUMMARY OF THE INVENTION

This invention relates to methods and apparatus for determining the concentration of a selected constituent of an individual's blood through analysis of a portion of the thermal radiation that an inner ear of the individual emits. In particular, the invention obtains the concentration of a particular constituent of interest by analyzing a portion of thermal radiation that originates from the individual's inner ear and passes through a cooled segment of the individual's tympanic membrane, thus revealing the absorption characteristics of various constituents of blood that flow through the membrane. The cooling of the tympanic membrane allows detection of these absorption characteristics which are undetectable if the membrane is at the same temperature as the inner ear cavity.

The use of the tympanic membrane rather than other tissue for obtaining the concentration of a particular constituent of blood flowing therein is advantageous because the tympanic membrane is thin and structurally simple. For example, the tympanic membrane contains less tissue than the finger tip, utilized by many disclosed non-invasive methods, and unlike the finger tip, it does not contain any bone structure. Accordingly, the radiation that passes through the tympanic membrane rather than the finger tip suffers less attenuation, thus resulting in a higher intensity of the transmitted radiation. In addition, the aforementioned properties of the membrane allow radiation over a large range of wavelengths to penetrate and be transmitted through the membrane, thus providing flexibility in selection of the wavelength of the illuminating radiation in a non-invasive testing apparatus.

The invention preferentially cools a selected portion of the tympanic membrane, thus producing a temperature differential between the inner ear and the membrane. This temperature differential allows employing the thermal radiation emanating from the inner ear for obtaining the absorption characteristics of selected constituents of blood flowing through the tympanic membrane. In particular, a portion of the radiation that originates from the inner ear passes through the cooled segment of the membrane. The passage of this radiation through the membrane results in absorption of a fraction of the radiation by various constituents of blood flowing therethrough. For example, the selected constituent may absorb a fraction of the thermal radiation at particular wavelengths. Thus, the transmitted radiation carries information regarding the selected constituent.

It should be understood that cooling of the tympanic membrane and in particular the periodic cooling of the membrane to create a lower temperature in the membrane than on the radiating surface of the inner ear is an important aspect of the present invention. In particular, in the absence of such a temperature differential, detection of the absorption spectrum of constituents of blood flowing through the membrane is very difficult. The cooling of the membrane accentuates the deviation of the spectrum of the radiation reaching the ear cavity after passing through the membrane from that of a black body, thus rendering detection of such a deviation feasible. One advantage of cooling of the membrane is providing a degree of thermal differentiation between the radiation source, i.e., the inner ear, and the absorbing sample, i.e., the tympanic membrane. This thermal differentiation allows direct measurement of the absorption spectra of various constituents and also allows a better determination of the absorbing pathlength, a parameter used to obtain the concentration of a selected constituent. The result of providing a degree of thermal differentiation between the inner ear and the tympanic membrane is effectively similar to implanting an external radiation source behind the tympanic membrane. In other words, the temperature differential between the inner ear and the tympanic membrane allows the inner ear to be utilized as such a radiation source.

One preferred embodiment of the invention cools a portion of the tympanic membrane by employing a cooled detector assembly and an optical imaging system that guides the radiation that emanates from the membrane onto the cold surface of the detector. Accordingly, this embodiment cools the membrane by a radiative transfer of heat from the membrane to the cold surface of the detector.

This radiative cooling can be further understood by first noting that it is well-known in physics that all bodies emit electromagnetic radiation in a range of wavelengths and intensities that are characteristic functions of their temperatures. Accordingly, both the surface of the detector and the inner ear cavity emit photons into the environment and also absorb a fraction of those photons in the environment that strike them. The exchange of photons between the cold surface of the detector and the warmer tympanic membrane causes the cooling of the membrane. The tympanic membrane cools more rapidly than the inner ear cavity because of its smaller thermal mass, thus resulting in a much lower temperature of the membrane compared to that of the inner ear.

The invention produces a periodic modulation of the temperature of the tympanic membrane such that during a portion of a measurement cycle the temperature of the membrane is lower than that of the inner ear cavity. In one embodiment, the periodic opening and closing of a shutter that is disposed between the tympanic membrane and the cold surface of a cooled detector exposes the tympanic membrane alternatively to the cold surface of the detector and the less emitting surface of the shutter, thus providing a modulation of the temperature of the membrane. The tympanic membrane follows the periodic temperature variation more easily than the inner ear because the thermal mass of the membrane is much smaller than that of the inner ear. The invention selects the rate of the periodic opening and closing of the shutter such that it produces a measurable temperature modulation of the membrane but does not cause significant temperature variations of the inner ear, i.e., the inner ear remains substantially at the body temperature. The periodic rate of opening and closing of the shutter can also be chosen in an apparatus according to the invention such that it does not interfere with the observation of the natural pulsatile variations of blood volume in the membrane. This observation helps discriminate arterial analytes from the non-arterial background.

The invention employs the portion of the thermal radiation emitted by the inner ear that passes through the cooled segment of the tympanic membrane to determine the concentration of a selected constituent of a patient's blood. In order to better understand how the invention achieves its objectives, one can model the tympanic membrane as a thin layer of tissue that is well-supplied by blood and is located in front of the tissue of the inner ear. The inner ear is warmer than the tympanic membrane and emits radiation in all directions with wavelengths and intensities that are characteristic functions of its temperature. A portion of this radiation travels through this thin membrane. Some constituents of blood flowing through the membrane absorb a fraction of the radiation that travels through the membrane at selected wavelengths. Thus, the radiation that emerges from the membrane exhibits absorption characteristics of said constituents.

It is clear to those skilled in the art that the interaction of the thermal radiation originating in the inner ear with the tympanic membrane is more complex than the simple model, described above, suggests. For example, the radiation that passes through the cold segment of the membrane suffers some scattering. Thus, the photons reaching the ear cavity are not all traveling in parallel paths. In fact, a cone of radiation emerges from the tympanic membrane.

The invention employs a variety of optical devices, inserted into the auditory canal of a subject, to collect and to guide the radiation that is transmitted through the cold segment of the membrane onto a detection device, e.g., an infrared detector. For example, in one embodiment of the invention, two lenses disposed at the two ends of a hollow tube form a classical imaging system for focusing a portion of the transmitted radiation on the detector. In particular, this device is inserted into the auditory canal such that one lens faces the cold segment of the tympanic membrane at a distance which is approximately equal to its focal length. This lens substantially collimates the radiation that originates from the inner ear and reaches the auditory canal after passing through the cold segment of the tympanic membrane. The second lens converges this substantially collimated beam onto the detection device.

Another embodiment of the invention employs one lens disposed between the tympanic membrane and an infrared detector to focus a portion of the transmitted radiation onto the detector. Some other embodiments of the invention employ at least one optical fiber disposed between the tympanic membrane and a detector such that the fiber receives a portion of the transmitted radiation at one end and transmits the received radiation to its opposite end to be delivered to the detector.

The invention can also employ a combination of optical fibers and lenses to guide the thermal radiation from the inner ear cavity to a detector. In particular, one embodiment utilizes an optical fiber disposed between the tympanic membrane and a detector to guide the transmitted radiation onto the detector and a lens disposed between the end of the fiber facing the membrane and the cooled segment of the membrane to couple the radiation into the fiber. In certain other embodiments, a lens disposed between the tympanic membrane and an optical fiber couples the radiation into the fiber. The fiber transmits the radiation to its opposite end, and a second lens disposed between the opposite end of the fiber and an infrared detector focuses the radiation leaving the fiber onto the detector.

The invention typically employs an infrared detector as a detection device to produce an electrical signal in response to the portion of the emitted radiation from the inner ear that reaches the detector after passing through the tympanic membrane. Some embodiments of the invention utilize a cooled detector that acts both as a means for detecting the radiation and also as a means for cooling the tympanic membrane. Because the detectivity of an infrared detector ("D*") typically increases as its temperature decreases, the use of a cooled detector improves the signal to noise ratio, thus improving the accuracy of the derived value of the concentration of the constituent of interest. Thus, the dual use of a detector both as a cooling means and also a detection means not only provides for a more compact apparatus but also improves the accuracy of the derived concentration. Such embodiments typically employ a shutter disposed between the tympanic membrane and the detector to change the temperature of the membrane in a periodic fashion by alternatively exposing the membrane to the cold surface of the detector and the surface of the shutter that is warmer than that of the detector.

As described previously, the tympanic membrane provides flexibility in selection of the wavelength of the illuminating radiation because the membrane is thin and allows transmission of radiation over a large range of wavelengths. This flexibility allows selection of long-wavelength radiation at which certain constituents may exhibit sharp absorption features and less overlap of absorption bands of various constituents, thus rendering the analysis of the data simpler than in shorter wavelengths, e.g., the near infrared region of the electromagnetic spectrum.

The invention can employ classical spectroscopic techniques to obtain and analyze the spectral features of a selected constituent when the constituent exhibits sharp spectral features with minimal overlap with absorption bands of other constituents. In the classical spectroscopic techniques, herein referred to as "Spectrophotometric Techniques," the intensity of transmitted radiation through a sample is typically obtained wavelength by wavelength by scanning the wavelength of a radiation source. Because the invention employs the broad band radiation emitted by the inner ear rather than an external radiation source, the wavelength by wavelength scanning of the radiation is not practical. The transmitted radiation, however, can be dispersed, for example by an appropriate grating or an infrared interferometer in a manner well-known in the art, to obtain a classical infrared spectrum, indicating transmission intensity as a function of wavelength. Such a spectrum can then be utilized, in a manner described above, to derive the concentration of the constituent of interest.

Another Spectrophotometric Technique, herein referred to as Filter Photometry, utilizes a plurality of infrared filters with non-overlapping transmission responses. Each filter can be disposed in front of an infrared detector to obtain the intensity of the radiation incident on the detector in a particular range of frequency. A plurality of measurements with a number of such filters provides a set of intensity data corresponding to a number of non-overlapping spectral regions that can be utilized, in a manner well-known in the art, to derive the concentration of a constituent of interest.

The present invention also contemplates the use of Fourier Transform Infrared Spectroscopy ("FTIR"), a well-known Spectrophotometric Technique, for deriving the concentration of the constituent of interest. FTIR utilizes the interference between a reference radiation beam and a beam of radiation transmitted through a sample containing a selected constituent to obtain the infrared spectrum of the constituent. After obtaining the spectrum of the constituent, the concentration of the constituent can be derived by analysis of the intensities of the spectral lines. Mark A. Arnold and Gary W. Small, Determination of physiological level of glucose in an aqueous matrix with digitally filtered Fourier transform infrared spectra, Analytical Chemistry, vol. 92, No. 14, July 17, 1990.

The practice of the invention, however, is not limited to employing Spectrophotometric Techniques. Many constituents of blood exhibit broad absorption bands that overlap with absorption bands of various other constituents. The Spectrophotometric Techniques are not appropriate for obtaining the concentration of such constituents. Accordingly, in such cases the invention employs an approach similar to those disclosed in U.S. Pat. Nos. 5,424, 545 and 5,321,265 for correlating the concentration of a particular constituent with the intensity of the radiation transmitted through the tympanic membrane. Such an approach, herein referred to as a Kromoscopic Technique, exploits analogies with color perception to extract the concentration of a particular constituent through examination of the global structure of its absorption band rather the positions of its absorption peaks. In particular, a Kromoscopic Technique creates a vector whose different components relate to the measured intensity of the transmitted radiation in a particular range of wavelengths. This vector is then utilized to derive the concentration of a selected constituent.

The invention may implement a Kromoscopic Technique by utilizing an infrared detector that is responsive to infrared radiation over a broad range of wavelengths and a multiplicity of infrared filters. Each filter is chosen to transmit infrared radiation over a range of a few hundred nanometers with a preferential transmission at a particular wavelength. In addition, the "tail" of the transmission response of each filter partially overlaps with that of at least one other filter. The data corresponding to multiple measurements of the intensity of the emitted radiation, each taken with a different filter disposed between the tympanic membrane and the detector, is sent to a computer, a hard-wired logic unit, or a neural network for analysis.

Thus, the invention attains the objectives set forth above by measuring the emitted radiation from the inner ear, having passed through a cold segment of the tympanic membrane and thus exhibiting the absorption characteristics of certain constituents of blood at various wavelengths. In particular, apparati according to the invention can be utilized to determine the concentration of many substances, e.g., glucose, in an individual's blood. In addition, the invention does not require that the concentration of a particular constituent be measured directly. In some cases, the measurement of the concentration of one substance can be derived by correlating it to a direct measurement of the concentration of another substance.

These and other features of the invention are more fully set forth below with reference to the detailed description of illustrated embodiments, and the accompanying drawings.

DETAILED DESCRIPTION

The invention measures the concentration of a particular constituent of interest in a subject's blood by cooling a segment of the subject's tympanic membrane to provide a temperature differential between the membrane and the inner ear and by analyzing a portion of the thermal radiation that originates in the subject's inner ear and passes through the cold segment before reaching the external auditory canal.

Figure 1:
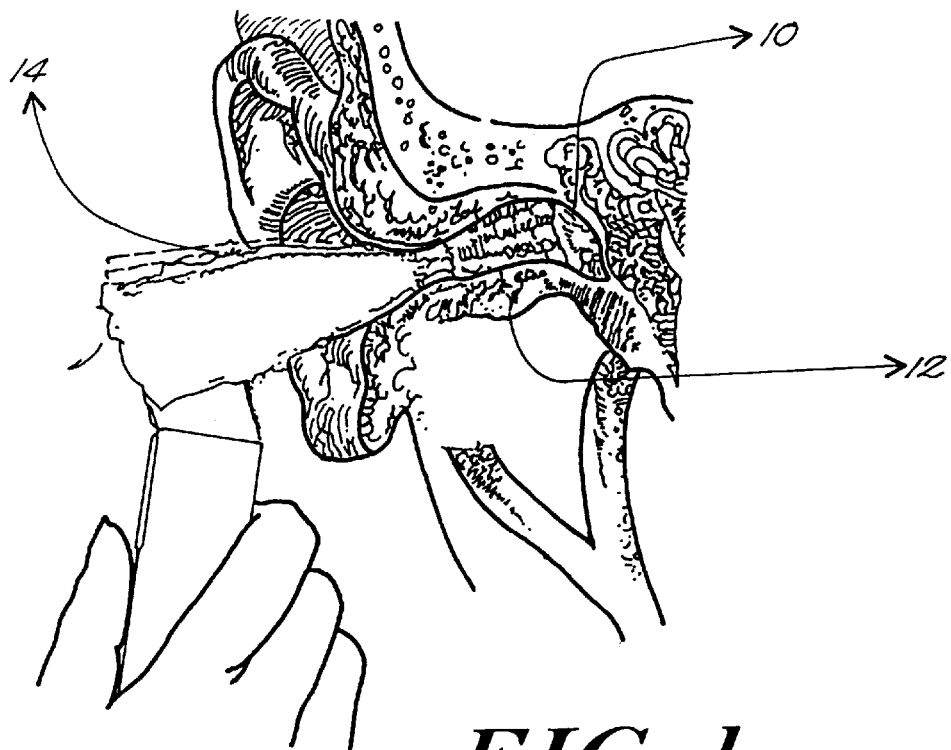
FIG. 1 illustrates a schematic drawing of selected parts of a human ear.

The invention can be more fully understood by referring to FIG. 1 which is a sketch of a portion of a human ear. The figure shows a tympanic membrane 10, an auditory canal 12, and a probe 14 that is inserted into the auditory canal facing the tympanic membrane. The probe, which is more fully described below in connection with various embodiments of the invention, can be utilized to cool the membrane and to collect the infrared radiation emitted by the inner ear.

Figure 2:
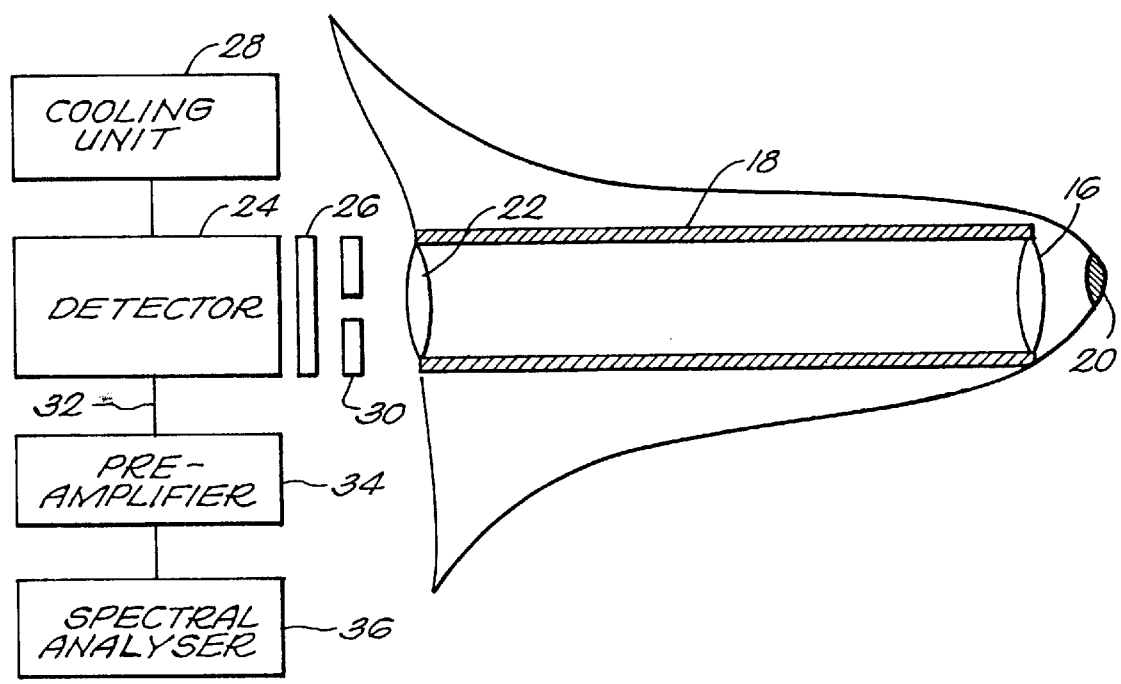
FIG. 2 is an apparatus according to the invention that employs a cooled infrared detector as both a means for cooling the tympanic membrane and also as means for detecting the thermal radiation emitted by the inner ear.

The various components of the probe in connection with one preferred embodiment of the invention are depicted in FIG. 2. A lens 16 that allows transmission of infrared radiation, e.g., a calcium fluoride lens, is disposed at the distal end of a hollow tube 18 that is inserted into the ear cavity, and faces a tympanic membrane 20. Another lens 22 that is also transparent to infrared radiation is placed at the proximal end of the tube.

The combination of the two lenses images a portion of the tympanic membrane onto the surface of a cooled infrared detector 24 that is placed outside the ear cavity. An infrared filter 26 is positioned in front of the detector to allow the passage of a portion of the radiation having a wavelength in a selected range. The preferred embodiment employs a number of such infrared filters with partially overlapping transmission responses to obtain a set of data from which the concentration of the constituent of interest is derived.

A cooling unit 28 keeps the infrared detector and the filter cold. In one implementation, both the filter and the detector are cooled through thermal contact with a cold reservoir. In another implementation, the cooling unit cools the detector thermoelectically while it cools the filter through contact with a cold reservoir.

A temperature controller 30 imposes a periodic temperature variation on the tympanic membrane. In one implementation, the temperature controller is a shutter that is disposed between the tympanic membrane and the infrared filter. The periodic opening and closing of the shutter exposes the tympanic membrane alternatively to the cold surfaces of the filter and the detector and the surface of the shutter which is warmer. During the times that the shutter is not covering the filter and the detector, the efficient transfer of heat from the tympanic membrane to the cold surface of the detector through the focusing effect of the lenses results in a preferential cooling of the membrane. The inner ear, however, does not cool as readily as the tympanic membrane, and remains substantially at the body temperature, i.e., approximately 37° C., and emits thermal radiation.

Figure 3:
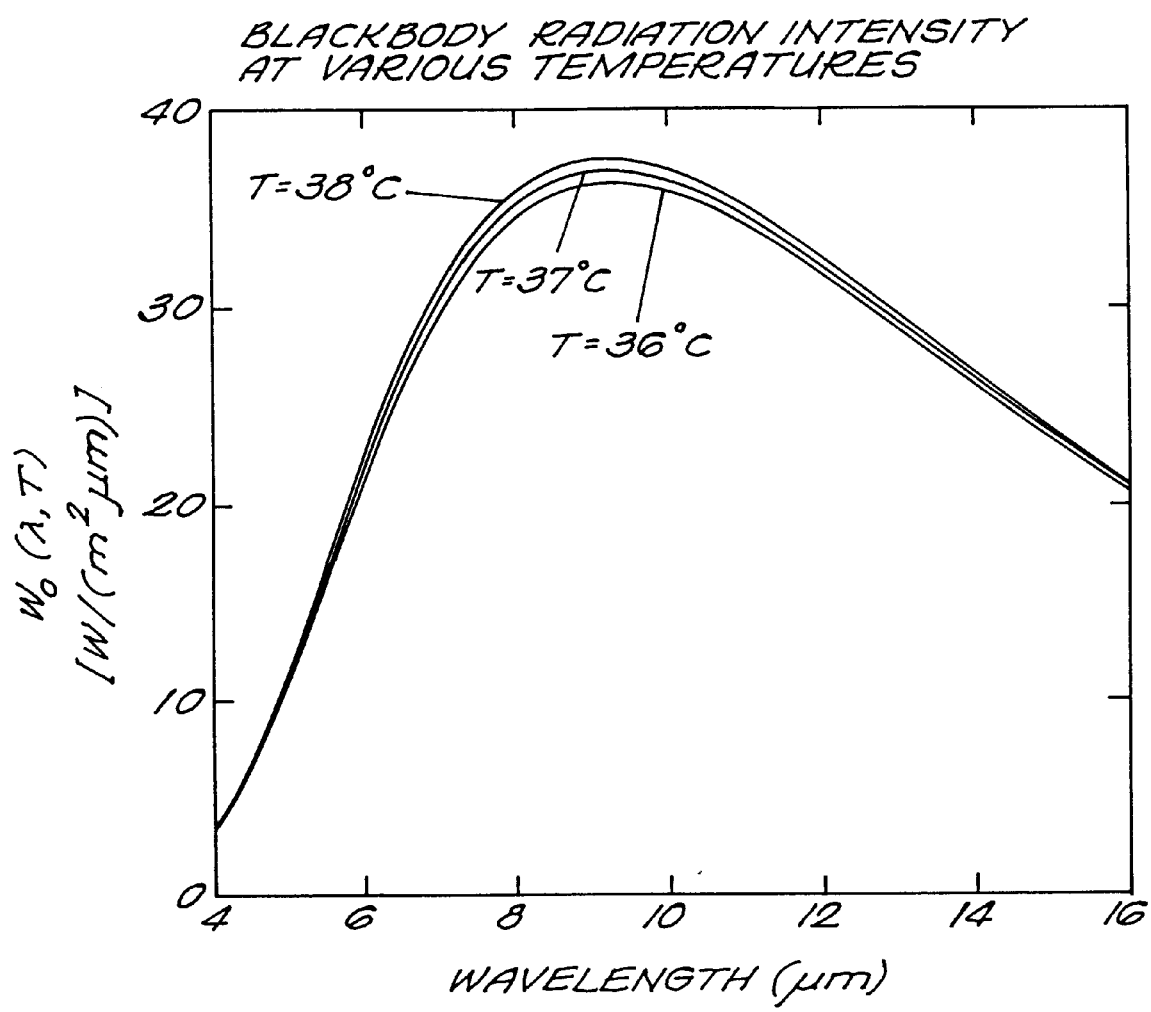
FIG. 3 shows the intensity of thermal radiation that an ideal "black body" at different temperatures emits as a function of wavelength.

It is well-understood in physics that all bodies emit electromagnetic radiation in a range of wavelengths and intensities that are characteristic functions of their temperatures. For example, FIG. 3, taken from U.S. Pat. No. 5,666,956, shows the intensity of thermal radiation that a "black body" emits as a function of wavelength at several temperatures close to the body temperature. Although the inner ear is not a perfect "black body," the intensity of its thermal radiation as a function of wavelength is qualitatively similar to the emission curve of FIG. 3.

Figure 4:
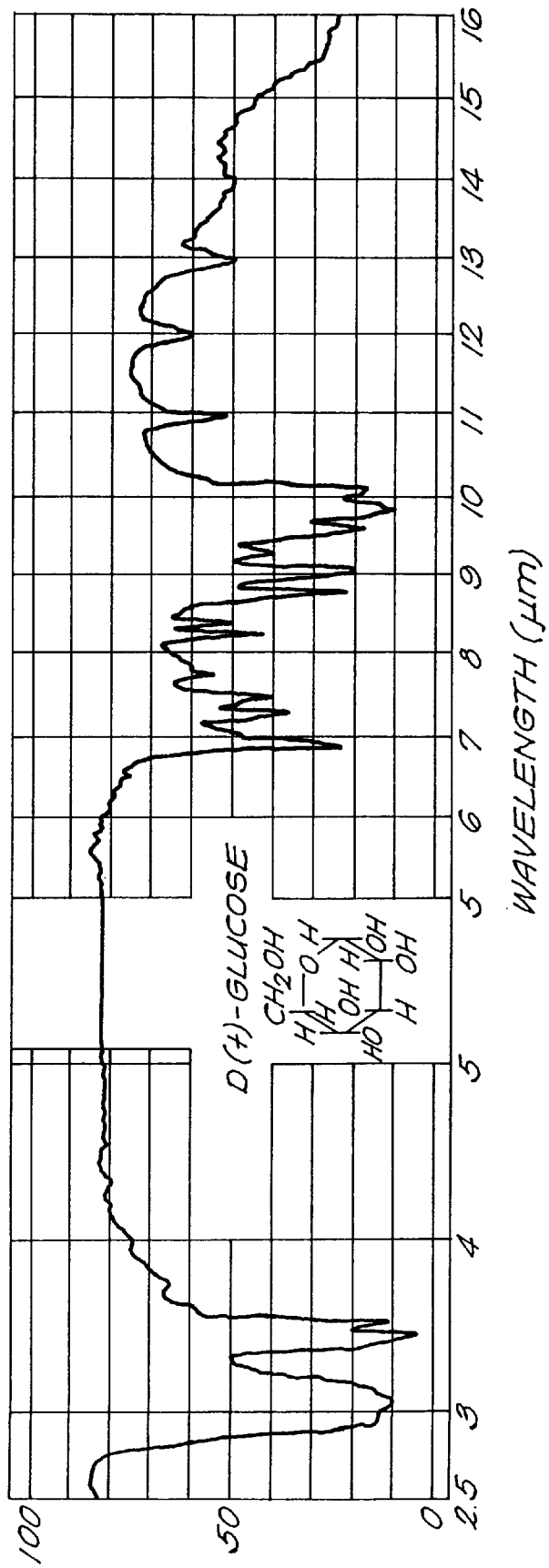
FIG. 4 is a portion of the infrared absorption spectrum of anhydrous D-glucose, illustrating a prominent absorption peak at 9.7 micron.
Figure 5:
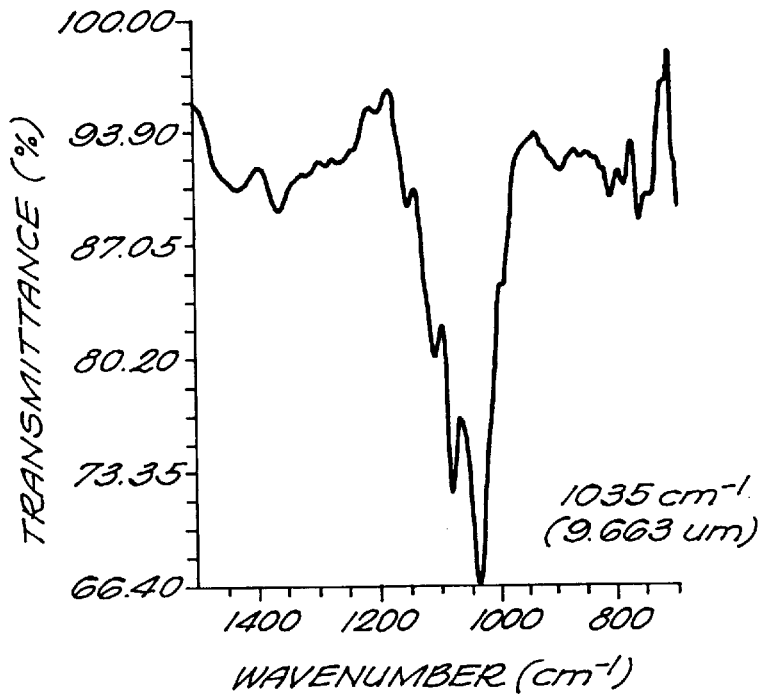
FIG. 5 shows a portion of the infrared spectrum of glucose in blood that illustrates, similar to the previous figure, an absorption peak at 9.7 micron.

The methods of the invention are particularly useful for determination of the concentration of those constituents of blood that exhibit absorption bands within a reasonable range of wavelengths in the vicinity of the wavelength at which the maximum intensity of thermal emission occurs. Accordingly, the methods of the present invention may be particularly suited for obtaining the concentration of D-glucose in a subject's blood because D-glucose exhibits a prominent absorption peak at 9.7 micron, understood to be the result of vibrational excitation of the carbon-oxygen-carbon bond in the pyrane ring of glucose, which approximately coincides with the wavelength at which the maximum intensity of thermal emission at body temperature occurs. FIG. 4. taken from an article by Mendelson et al., shows the infrared absorption spectrum of anhydrous D-glucose, illustrating the afore-mentioned absorption peak at 9.7 micron. Yitzhak Mendelson, Allen C. Clermont, Robert A. Peura, and Been-Chyuan Lin, Blood glucose measurement by multiple total reflection and infrared absorption spectroscopy, IEEE Transaction on Biomedical Engineering, vol. 37, No. 5, May 1990. FIG. 5, is a spectrum of glucose in blood, taken form the same article by Mendelson et al., obtained by employing the attenuated total reflection technique which also shows a prominent absorption peak at 9.7 micron.

Referring again to FIG. 2, the combination of the two lenses focuses a portion of the infrared radiation, having originated from the inner ear and having passed through the cold tympanic membrane, through the filter onto the detector. The filter allows transmission of a portion of the emitted radiation corresponding to a selected range of wavelengths. One implementation of the preferred embodiment employs a plurality of infrared filters such that the transmission range of each filter partially overlaps with that of at least one other filter to obtain a set of intensity data at various wavelength ranges.

The detector produces an electrical signal in response to the incident radiation. A number of electrical wires 32 carry this signal from the detector to a pre-amplifier unit 34 that receives the signal and transmits an amplified signal to a spectral analyzer 36 which stores the amplified signal for analysis. The spectral analyzer employs either the well-known Spectrophotometric Techniques of high resolution spectroscopy, or methods of analysis similar to those disclosed in the aforementioned U.S. Pat. Nos. 5,321,265, 5,434,412, and 5,424,545, i.e., Kromoscopy, to derive a value directly related to the concentration of the constituent of interest from the data. The choice of a technique for analysis of the transmitted radiation depends on whether the constituent of interest exhibits sharp or broad bands. The analyzer typically employs Spectrophotomctric Techniques for analysis of sharp features and Kromoscopic Techniques for analysis of broad features.

The preferred embodiment employs calibration curves to derive the concentration of a particular constituent of blood based on the value obtained by the spectral analysis of the signal as described above. For example, the calibration curve for a particular subject can be obtained by comparing the concentration derived by traditional invasive techniques, e.g., finger prick method, with the values derived by the methods of the present invention.

Figure 6:
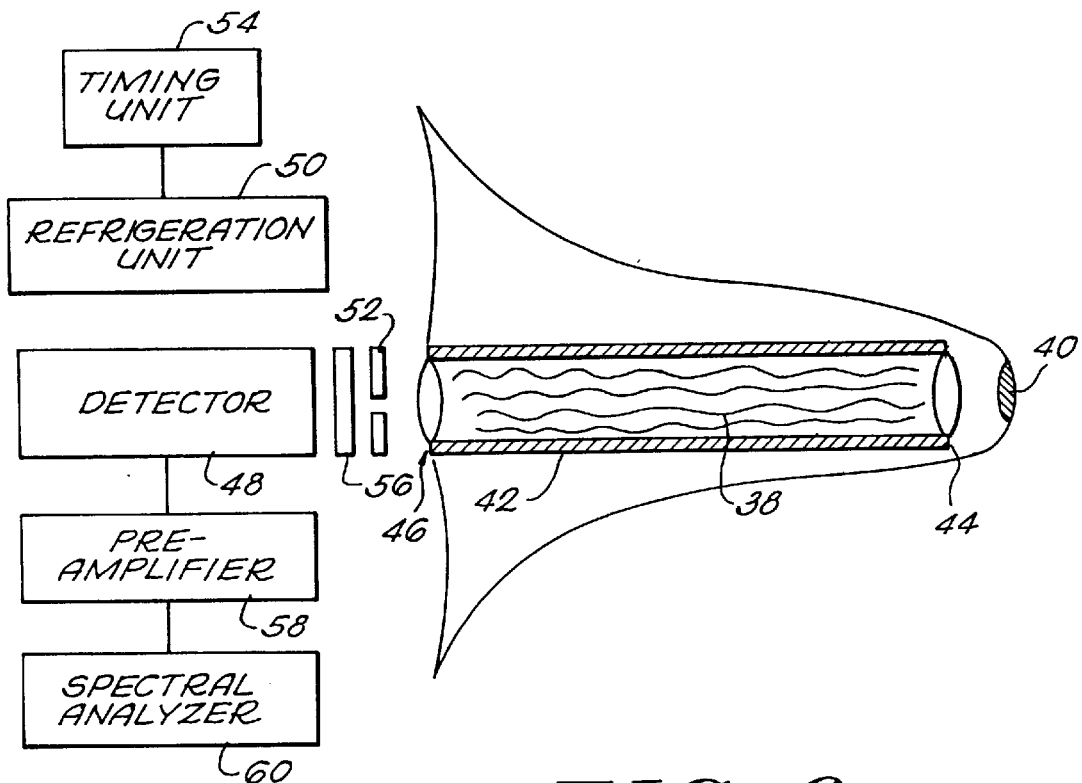
FIG. 6 illustrates an apparatus according to the invention that employs a cooled infrared detector for cooling a segment of the tympanic membrane, and it employs a bundle of optical fibers to transmit the radiation emitted by the inner ear that has passed through the cold segment of the membrane to the infrared detector.

FIG. 6 shows another embodiment of the invention that employs a bundle of optical fibers 38 to collect the infrared radiation that originates from the inner ear and passes through a cold segment of a tympanic membrane 40. In particular, the figure illustrates that the optical fibers are placed in the hollow center of a rod 42 which is inserted into the auditory canal such that one end of each optical fiber faces the tympanic membrane. In addition, a first lens 44 is disposed at the distal end of the rod between the tympanic membrane and the optical fibers in order to provide a more efficient coupling of the infrared radiation, emanated from the inner ear, into the fibers.

Further reference to the figure shows that a second lens 46, disposed at the proximal end of the rod, provides an efficient coupling of the radiation transmitted through the optical fibers onto an infrared detector 48.

This embodiment employs a refrigeration unit 50 to cool the surface of the infrared detector, which in turn, results in cooling of the segment of the membrane that two lenses image onto the cold surface of the detector. The opening and closing of a shutter 52 exposes the imaged segment of the membrane periodically to the cold surface of the detector, thus resulting in a periodic variation of the temperature of the membrane.

Further reference to FIG. 6 shows that this embodiment, similar to the previous one, employs a plurality of infrared filters 56 with partially overlapping spectral responses to allow transmission of a portion of the emitted radiation, having a selected range of wavelengths, onto the detector. A series of measurements, each taken with one of the filters, provides data corresponding to the intensity of the emitted radiation in various wavelength ranges. It should be understood that when the cold surface of the detector is utilized as a cooling means, the infrared filters disposed in front of the detector, are also cooled by the refrigeration unit.

The electrical signals, produced by the infrared detector in response to the incident radiation, is sent to a preamplifier 58 that, in turn, sends amplified signals to a spectral analyzer 60. The spectral analyzer examines the data for the absorption characteristics of a particular constituent by employing either Kromoscopic Techniques or traditional Spectrophotometric Techniques to derive the concentration of the particular constituent of interest. The choice of the spectral analysis technique depends on various factors including the breadth of the absorption bands of the constituent of interest, the degree of overlap among various absorption bands, the signal-to-noise ratio of the detected radiation, etc. The analyzer typically utilizes a Kromoscopic Technique if the absorption band is broad and featureless and overlaps with the absorption bands of other constituents.

In will thus be seen that the invention attains the objectives set forth above. The embodiments of the present invention are intended to be interpreted as illustrative and not in a limiting sense. Those skilled in the art shall be able to make numerous variations and modifications to the above embodiments without departing from the spirit of the invention.

Having described the invention, what is claimed as secure by Patent Letters is:

1. A method for determining the concentration of a constituent of interest in blood flowing through a tympanic membrane of a subject comprising the steps of:

inserting a radiation collection device into the external auditory canal of said subject to a position wherein there is an unrestricted optical path between a portion of the tympanic membrane and said device, periodically cooling a selected location lying within said portion of the tympanic membrane to a temperature lower than the temperature of the inner ear cavity during a measurement cycle, directing infrared radiation that originates in the inner ear and is transmitted through said selected location onto an infrared detection device with said collection device during said measurement cycle, obtaining an output signal produced by said infrared detection device in response to said directed infrared radiation, said output signal being related to the concentration of said constituent of interest, and deriving the concentration of said constituent of interest from said output signal.

2. The method of claim 1, wherein the step of directing said radiation comprises utilizing an imaging system to focus a portion of said transmitted radiation onto said infrared detection device.

3. The method of claim 1, wherein the step of directing said transmitted radiation comprises utilizing at least a lens disposed between the tympanic membrane and said infrared detection device, said lens focusing a portion of said transmitted radiation onto said infrared detection device.

4. The method of claim 1, wherein the step of directing said transmitted radiation comprises utilizing at least one optical fiber disposed between the tympanic membrane and said infrared detection device, said fiber collecting a portion of said transmitted radiation and directing said collected radiation to said infrared detection device.

5. The method of claim 4, further comprising the step of disposing a first lens between said optical fiber and the tympanic membrane to focus a portion of said transmitted radiation into said fiber.

6. The method of claim 5, further comprising the step of disposing a second lens between said optical fiber and said detection device such that said second lens focuses a portion of the radiation being transmitted through said fiber onto said detection device.

7. The method of claim 1, wherein the step of directing said transmitted radiation comprises disposing at least two lenses between the tympanic membrane and said detection device such that said selected location of the tympanic membrane lies substantially in the focal plane of a first lens and said infrared detection device lies substantially in the focal plane of a second lens, said first lens substantially collimating said transmitted radiation and said second lens receiving said collimated radiation and focusing it onto said detection device, whereby said lenses image a portion of said transmitted radiation onto said infrared detection device.

8. The method of claim 1, wherein the step of cooling said selected location of the tympanic membrane to a temperature lower than the temperature of the inner ear comprises utilizing a cooled infrared detector having a cold surface for cooling said selected location of the tympanic membrane.

9. The method of claim 1, further characterized by selecting said detection device to comprise an infrared detector being adapted to receive said directed radiation, a plurality of infrared filters adapted such that each filter can be individually disposed between the tympanic membrane and said detector, each of said filters transmitting infrared radiation in a selected range of wavelengths, whereby the output signal of said detector is proportional to the intensity of said directed radiation in a range of wavelengths associated with the transmission of said filter.

10. The method of claim 9, further characterized by selecting the range of wavelengths associated with the transmission of at least one of said filters to partially overlap with the transmission range of another of said filters.

11. The method of claim 10, wherein the step of deriving the concentration of said substance comprises utilizing Kromoscopic Techniques.

12. The method of claim 1, wherein the step of deriving the concentration of said substance comprises utilizing Spectrophotometric Techniques.

13. The method of claim 12, wherein said Spectrophotometric Techniques comprise Filter Photometry.

14. The method of claim 1, wherein said detection device comprises a Fourier Transform Infrared Spectrometer.

15. The method of claim 1, wherein said constituent of interest comprises glucose.

16. Apparatus for non-invasive determination of the concentration of a constituent of interest in blood flowing through a tympanic membrane of a subject comprising:

cooling means for periodically cooling a selected location of the tympanic membrane to a temperature lower than the temperature of the inner ear cavity during a measurement cycle, a radiation collection device, said device adapted to be inserted into the external auditory canal of said subject to a position such that there is an unrestricted optical path between said selected location and said device, whereby said device collects infrared radiation that originates in the inner ear and is transmitted through said selected location of the membrane, an infrared detection device adapted to receive a portion of the radiation collected by said collection device to produce an output signal, said signal being related to the concentration of said constituent of interest, and a spectral analyzer adapted to receive said output signal, said analyzer employing spectral analysis techniques to analyze said received output signal to obtain the concentration of said constituent.

17. The apparatus of claim 16, wherein said collection device comprises an imaging system for focusing a portion of said transmitted radiation onto said infrared detection device.

18. The apparatus of claim 16, wherein said collection device comprises a lens adapted to be disposed between the tympanic membrane and said detection device, said lens focusing a portion of said transmitted radiation onto said detection device.

19. The apparatus of claim 16, wherein said collection device comprises at least one optical fiber adapted to be disposed between the tympanic membrane and said infrared detection device, said fiber collecting a portion of said transmitted radiation and directing said collected radiation to said detection device.

20. The apparatus of claim 19, wherein said collection device further comprises at least a lens adapted to be disposed between said optical fiber and the tympanic membrane, said lens focusing said transmitted radiation into said fiber.

21. The apparatus of claim 20, wherein said collection device further comprises at least a second lens disposed between said optical fiber and said infrared detection device such that said second lens focuses a portion of the radiation being transmitted through said fiber onto said detection device.

22. The apparatus of claim 16, wherein said collection device comprises at least two lenses adapted to be disposed between the tympanic membrane and said detection device such that said selected location of the membrane lies substantially in the focal plane of one of said lenses and said infrared detection device lies substantially in the focal plane of another of said lenses, whereby said lenses image a portion of said transmitted radiation onto said infrared detection device.

23. The apparatus of claim 16, wherein said cooling means comprises a cooled infrared detector having a cold surface for cooling said selected location of the tympanic membrane.

24. The apparatus of claim 16, wherein said detection device comprises an infrared detector being adapted to receive said directed radiation, and a plurality of infrared filters adapted such that each filter can be individually disposed between the tympanic membrane and said infrared detector, each of said filters transmitting infrared radiation in a selected range of wavelengths, whereby the output signal of said detector is proportional to the intensity of said directed radiation in a range of wavelengths associated with the transmission of said filter.

25. The apparatus of claim 24, wherein the transmission range of at least one of said filters partially overlaps with the transmission range of another of said filters.

26. The apparatus of claim 16, wherein said infrared detection device comprises a Fourier Transform Infrared Spectrometer.

27. The apparatus of claim 16, wherein said infrared detection device comprises a detection device utilizing Spectrophotometric Techniques.

28. The apparatus of claim 16, wherein said infrared detection device comprises a detection device utilizing Kromoscopic Techniques.

29. The apparatus of claim 16, wherein said infrared detection device comprises a detection device utilizing Filter Photometry.

30. The apparatus of claim 16, wherein said constituent of interest comprises glucose.

\* \* \* \* \*